United States Patent
Motomura et al.

(10) Patent No.: US 8,317,020 B2
(45) Date of Patent: Nov. 27, 2012

(54) STORAGE RECEPTACLE FOR USED SUTURE NEEDLES

(76) Inventors: Tadashi Motomura, Houston, TX (US); Yasushi Takigawa, Moraga, CA (US); Hitoshi Sakuragi, Otsu (JP)

(*) Notice: Subject to any disclaimer, the term of this patent is extended or adjusted under 35 U.S.C. 154(b) by 142 days.

(21) Appl. No.: 12/909,679

(22) Filed: Oct. 21, 2010

(65) Prior Publication Data

US 2011/0167768 A1    Jul. 14, 2011

Related U.S. Application Data

(63) Continuation-in-part of application No. 12/686,373, filed on Jan. 12, 2010, now Pat. No. 8,074,797.

(51) Int. Cl.
   *B65D 83/10* (2006.01)

(52) U.S. Cl. ............ 206/366; 248/205.3; 206/380

(58) Field of Classification Search .......... 206/366, 206/365, 364, 380, 381, 460, 63.5, 495, 813, 206/484, 63.3, 339, 820; 66/5, 6, 17; 248/205.3
   See application file for complete search history.

(56) References Cited

U.S. PATENT DOCUMENTS

| | | | | | |
|---|---|---|---|---|---|
| 2,897,962 | A | * | 8/1959 | Zackheim | 206/369 |
| 3,759,376 | A | * | 9/1973 | Lisowski | 206/388 |
| 4,105,115 | A | * | 8/1978 | Horvath et al. | 206/370 |
| 4,182,448 | A | * | 1/1980 | Huck et al. | 206/380 |
| 4,260,056 | A | * | 4/1981 | Horvath et al. | 206/370 |
| 4,344,532 | A | * | 8/1982 | Eldridge et al. | 206/370 |
| 5,538,132 | A | * | 7/1996 | Propp et al. | 206/365 |
| 5,819,918 | A | * | 10/1998 | Scanlon | 206/63.3 |
| 2002/0088728 | A1 | * | 7/2002 | Sugama | 206/370 |

* cited by examiner

*Primary Examiner* — Bryon Gehman
*Assistant Examiner* — Rafael Ortiz
(74) *Attorney, Agent, or Firm* — Rutan & Tucker, LLP

(57) ABSTRACT

A method for disposing of suture needles. The method includes attaching the needle storage receptacle to a mounting surface by positioning a first adhesive surface against the mounting surface, peeling back a strip of protective material from a second adhesive surface of a needle storage unit and placing a suture needle between the protective material and the second adhesive surface, removing the protective material from the second adhesive surface and a third adhesive surface adjacent the second adhesive surface, and folding the second adhesive surface into contact with the third adhesive surface to permanently trap the needle.

5 Claims, 8 Drawing Sheets

STEP 500
(before
folding)

STEP 500
(after folding)

STEP 502

STORAGE RECEPTACLE FOR USED SUTURE NEEDLES

PRIORITY

This application is a continuation-in-part of U.S. patent application Ser. No. 12/686,373, filed Jan. 12, 2010, now U.S. Pat. No. 8,074,797, which is incorporated by reference in its entirety into this application.

BACKGROUND

1. Technical Field

The present invention relates to a needle-storage receptacle with which needles used in suturing in the operating room are encased in adhesive tape to allow the needles to be disposed of easily and safely, and, having encased the needles, on which numerals appear on the surface, facilitating the handling of a number of used needles.

2. Description of the Related Art

Consumable implements employed in surgery mandate strict administration in terms of the correspondence between the number brought into the operating area and the number following surgery. In an operation, if correspondence between the number brought into the operating area and the number following surgery cannot be obtained, giving rise to a suspicion of loss, the possibility that a needle(s) has been left in the patient will be suspected. which hangs up final suturing until the needle(s) is discovered, incurring delays in the operating time. This proves to be a significant burden on the patient and on the physicians and nurses who perform the surgery.

Meanwhile, suture needles employed in surgery are prepared in accordance with an operation and handled after suture by being placed on a tray, separated from the unused needles, wherein a problem has been that during the surgery, medical accidents in which physicians and nurses come into contact with and are pricked by the used needles occur.

Therein, the inventors devised the present needle receptacle so as not only to case the handling and disposal of a number of suture needles that have been used in surgery, helping contribute to alleviating the labor of physicians and nurses, but also to prevent in the operating area medical accidents with physicians and nurses due to used needles.

BRIEF SUMMARY

An object of the present invention is to make available a needle storage receptacle that serves to render safe and simple the handling and disposal of a number of suture needles that have been used in surgery, and that serves to prevent medical accidents with physicians and nurses in which they come into contact with and are pricked by used needles.

The invention as given in a first aspect is a needle storage receptacle for safely storing and disposing of used suture needles in the operating room, and is characterized in that: the needle storage receptacle has a plurality of needle-storing units and film-anchoring portions: each needle-storing unit is furnished with a mounting pad for adhering a used suture needle, a lid part for covering the mounting pad, and a grip tab in order that the lid part may be grasped when the needle storing unit is to be open/closed; the mounting pads and the lid parts are made from sheeting, between the mounting pads and the lid parts is a fold line or score, and the mounting pads have adhesive surfaces on the front side and the rear side: the lid parts have an adhesive surface on the front side, and on the rear side are printed with numerals in such a way as to enable their recognition as numerals when the lid parts are overlaid onto and stuck together with the mounting pads; and the film-anchoring portions are structures provided on both of right-and-left ends of the needle storage receptacle.

The invention as given in a second aspect is a needle storage receptacle for safely storing and disposing of used suture needles in the operating room, and is characterized in that: the needle storage receptacle has a plurality of needle-storing units and film-anchoring portions; each needle-storing unit is furnished with a mounting pad for adhering a used suture needle, a lid part for covering the mounting pad, and a grip tab whereby the lid part is grasped when the needle storing unit is open/closed; the mounting pads and the lid parts are made from sheeting, between the mounting pads and the lid parts is a fold line or score, and the mounting pads have adhesive surfaces on the front side and the rear side; the lid parts have an adhesive surface on the front side, and on the rear side are printed with numerals in such a way as to enable their recognition as numerals when the lid parts are overlaid onto and stuck together with the mounting pads; adjoining needle-storing units each have a gap between them; and the film-anchoring portions are structures provided on either right-and-left ends of the needle storage receptacle.

The invention as given in a third aspect is the needle storage receptacle as given in the first or second aspects, characterized in that the rear side of the lid parts are not printed with numerals.

The invention as given in a fourth aspect is the needle storage receptacle as given In any of the first through third aspects, characterized in that the grip tabs of the needle-storing units have an elevated structure providing a slight angle from the plane containing the mounting pads and the lid parts, so as to ease gripping and opening/closing of the needle storing units.

The invention as given in a fifth aspect is the needle storage receptacle as given in any of the first through fourth aspects, characterized in that the sheeting employed in each needle-storing unit may be semitransparent, translucent white, or opaque.

The invention as given in a sixth aspect is the needle storage receptacle as given in any of the first through fifth aspects, characterized in that rather than having a plurality of linked needle-storing units, it has a singular unit.

Utilizing a needle storage receptacle involving the present invention readily can: realize eased handling of a number of suture needles that have been used in surgery; realize alleviation of the burden on patients due to prolongation in the length of an operation, associated with the intricacies of handling a number of needles; and realize prevention of medical accidents with physicians and nurses, in which they come into contact with and are pricked by used needles in the operating area.

DETAILED DESCRIPTION

Below, with reference to the drawings. an explanation of best modes for embodying the present invention will be made.
Embodying Mode I.
Embodying Mode 1

Embodying Mode 1 is a needle storage receptacle in which a predetermined number of needle-storing units composed of a mounting pad that adheres a used suture needle that has been used in surgery, a lid part that is overlaid onto the mounting pad to cause the needle to cling to the pad, and a grip tab that is used in opening/closing the lid part are linked.

Figure 1:
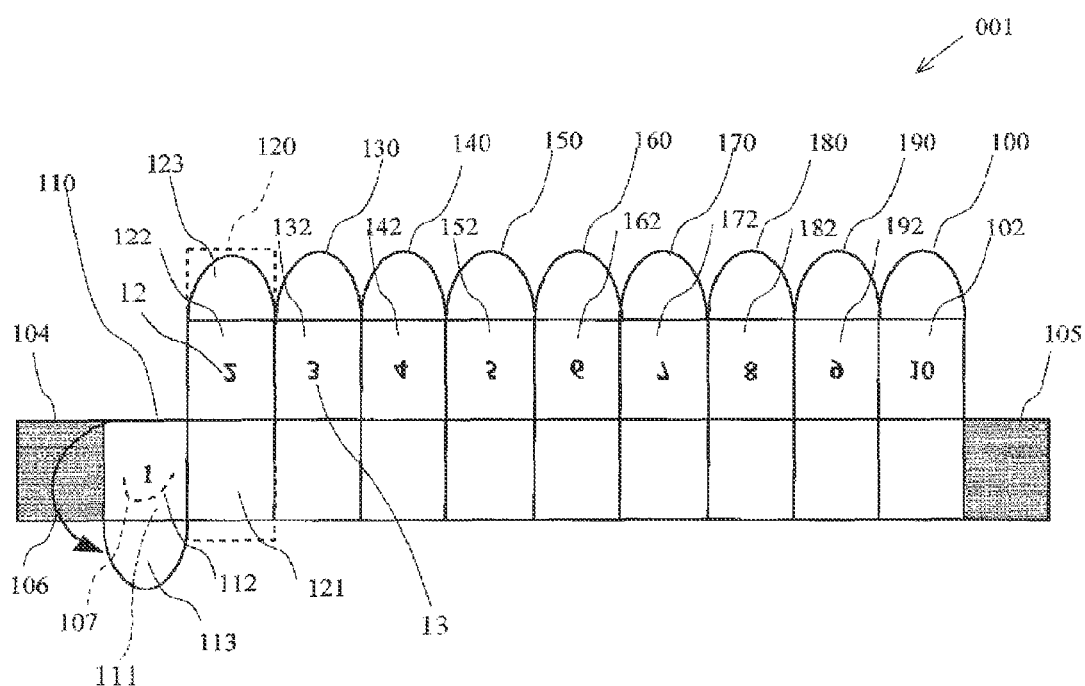
FIG. 1 is a plan view depicting a general outline of the configuration of a needle storage receptacle, composed of a plurality of needle-storing units, involving Embodying Mode I.

Reference is made to FIG. 1, a plan view depicting a general outline of the configuration of a needle storage receptacle. composed of a plurality of the needle-storing units. involving Embodying Mode I.

The needle-storing units in FIG. 1 are made from sheeting, wherein, in order from the left, ten units—110 (in FIG. 1, a state in which the grip tab and the lid part have been folded over onto the mounting pad is illustrated), 120, 130, 140, 150, 160, 170, 180, 190, and 100—are linked, and further, film-anchoring portions 104 and 105 are provided on both the left and right ends, constituting a needle storage receptacle 001. It will be appreciated that the number of needle-storing units in the connected series is not limited to ten.

The needle-storing unit 120 is furnished with a mounting pad 121 that adheres a used suture needle, a lid part 122 that is overlaid onto the mounting pad, and a grip tab 123 in order that the lid part may be grasped when the needle storing unit is to be open/closed, with the other needle-storing units having the same structure. As illustrated at needle-storing unit 110, the grip tab 113 is grasped to fold the lid part 112 over as indicated by the arrow 106 and lay it onto the mounting pad 111, encasing a needle inside, whereby the needle is securely captured adhesively and stored between the adhesive surfaces of the lid part 112 and the mounting pad 111. In some examples, multiple needles may be securely captured adhesively and stored between the adhesive surface of the lid part 112 and the mounting pad 111. For example, two needles might be securely captured in this way. Additional needles might be captured between the adhesive surface of the lid part 112 and the mounting pad 111, but in some cases this can be too bulky. Accordingly, one to two needles captured adhesively and stored between the adhesive surface of the lid part 112 and the mounting pad 111 may be preferable.

On the lid part of each needle-storing unit, in order from the left, 112 (in FIG. 1, it is laid onto the mounting pad 121), 122, 132, 142, 152, 162, 172, 182, 192, and 102, the numerals "1," "2," "3," "4," "5," "6," "7," "8," "9" and "10" are printed as display numbers. On the rear side of the lid part of each needle-storing unit, so that when each grip tab is grasped to fold the lid part over and stick it onto the mounting pad and seal a needle inside, a numeral can be read from the front side. Reference mark 12 shows where the display numeral "2" has been printed, while reference mark 13 shows where the display numeral "3" has been printed. It will be appreciated that with numerals printed on the lid rear side in implementations in which the constituent film is transparent, through the front side recognition of numerals appearing vertically symmetrical would be possible. It will be understood that, in an embodiment that is intended to capture and store multiple needles, e.g., two, adhesively between the adhesive surface of the lid part 112 and the mounting pad 111 a combination of numerals might be sued, e.g., numerals "1/2," "3/4," "5/6" "7/8," etc.

In addition, the film-anchoring portions 104 and 105, provided on both the right and left ends, are utilized in instances in which the adhesive force provided on the underside portion of the mounting pad of each needle-storing unit has weakened. For example, the film-anchoring portions 104 and 105 might be utilized when the adhesive forces have weakened such that the anchoring of the needle-storing units onto the sheet over the scrub nurse's instrument stand is insufficient, or in instances in which the adhesive surface on the rear side of the mounting pad has peeled off. Additionally, the anchoring portions 104 and 105 can be grasped with forceps to reinforce the anchoring of the needle storage receptacle. Also, the sheeting employed in the film-anchoring portions 104 and 105 may be a colored film, distinct from the color of the sheeting employed in the needle-storing units.

Figure 2:
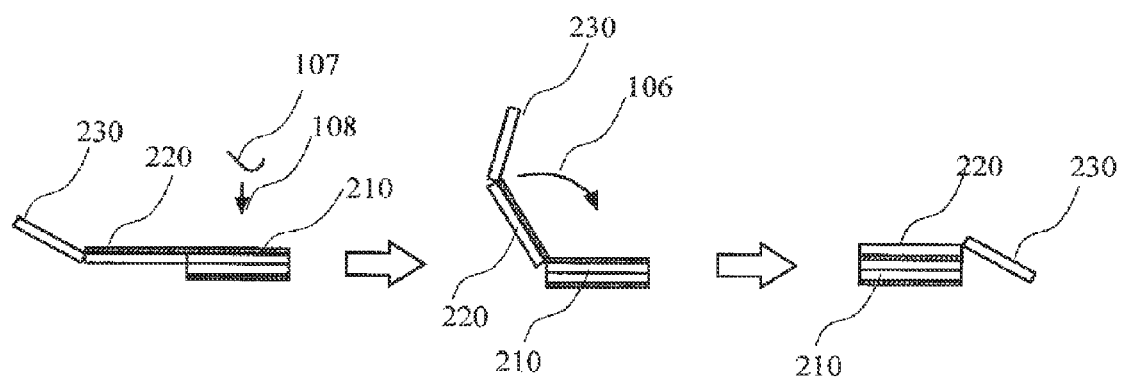
FIG. 2 is an explanatory diagram for explaining a method of sealing a used needle into a needle-storing unit.

Reference is made to FIG. 2, an explanatory diagram for describing how a used needle is sealed inside a needle-storing unit.

A needle 107 that is to be discarded is, as indicated by the arrow 108 in the figure, placed onto the front-side portion of the mounting pad 210. Next the grip tab 230 is grasped to lift the lid part 220 and, as indicated by the arrow 106, the lid part 220 is folded over and laid onto the mounting pad 210. By the film of the lid part and of the mounting pad adhering and closing shut, the needle 107 is completely sealed inside.

Figure 3:
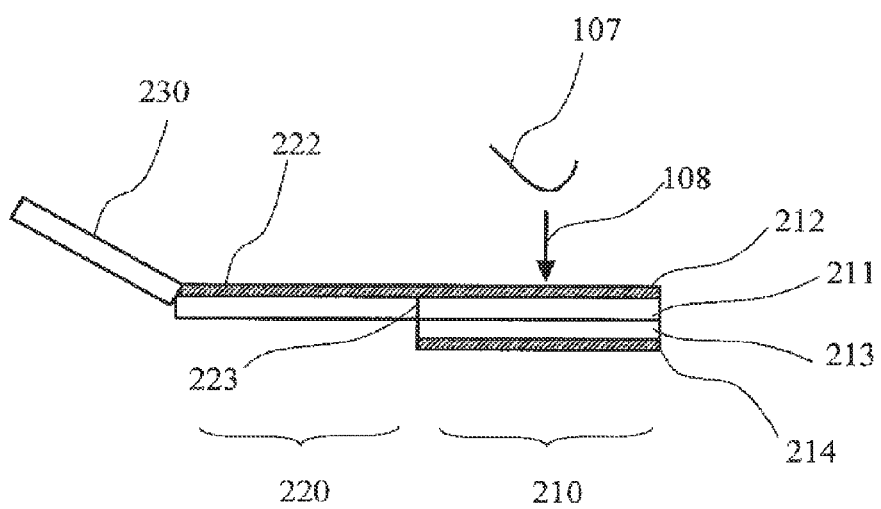
FIG. 3 is an explanatory side-view diagram for explaining a needle-storing unit where a used needle clings and is stored.

Reference is made to FIG. 3, a side-view diagram of the needle-storing unit in FIG. 2. The needle-storing unit has the lid part 220, the mounting pad 210, and the grip tab 230, with an adhesive surface 222 being provided on the front-side portion of the lid part 220, and with a fold line or score 223 being provided in between the mounting pad 210 and the lid part 220, facilitating folding of the unit.

The mounting pad 210 is provided on its front-side portion 211 with an adhesive surface 212 for adhering a used needle 107 and the lid part 220, and is provided on its underside portion 213 with an adhesive surface 214 so that the needle-storing unit may be anchored for example to the sheet covering the instrument tray.

Embodying Mode 2

Figure 4:
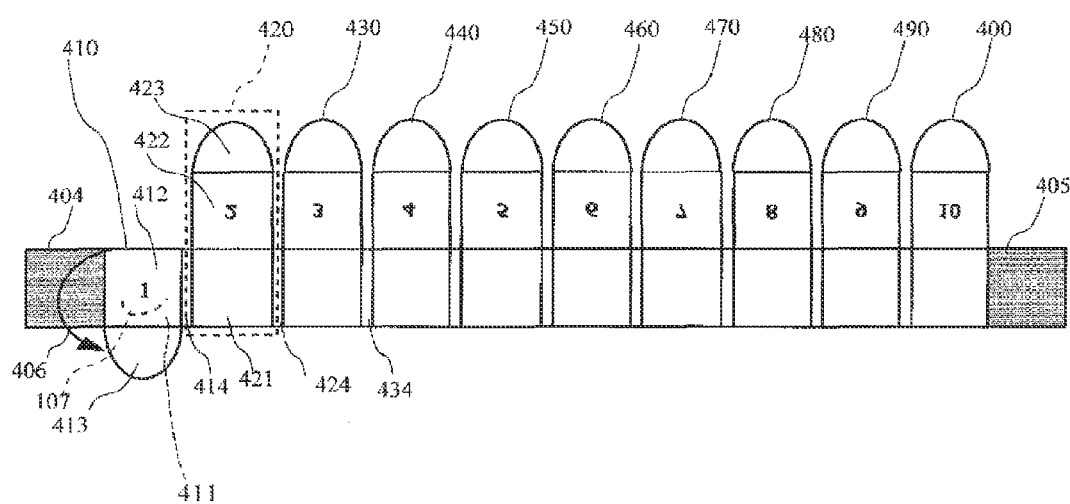
FIG. 4 is a plan view depicting a general outline of the configuration of a needle storage receptacle, composed of a plurality of needle-storing units. involving Embodying Mode 2.

Reference is made to FIG. 4, a plan view depicting a general outline of the configuration of a needle storage receptacle, composed of a plurality of needle-storing units, involving Embodying Mode 2.

The needle storage receptacle involving Embodying Mode 2, different from the needle storage receptacle of Embodying Mode I, possesses a structure in which needle-storing units are linked, with each flanking a gap between it and the needle-storing unit that it adjoins. Ensuring the stability of the needle storage receptacle overall is therefore easier by comparison to the situation with the needle storage receptacle of Embodying Mode I. In particular, in implementations in which the adhesive used on the adhesive surfaces is soft, even if the needle storage receptacle is subjected to external forces from various directions when being kept stored or during transport, the gaps opening between any two needle-storing units help prevent risk of any two neighboring needle-storing units becoming stuck together.

The needle storage receptacle involving Embodying Mode 2 is composed of a plurality of needle-storing units and the needle-storing units are made from sheeting, and in between adjoining needle-storing units the respective gaps are provided, forming a structure in which the needle-storing units are linked. In order from the left, ten units—410 (in FIG. 4, a state in which the grip tab and the lid part have been folded over onto the mounting pad is illustrated), 420, 430, 440, 450, 460, 470, 480, 490, and 400—are linked. Each pairs of units, respectively, may flank a gap. Further, film-anchoring portions 404 and 405 are provided on both the left and right ends, constituting a needle storage receptacle. It will be appreciated that the number of needle-storing units in the connected series is not limited to ten.

The needle-storing unit 420 is structured having a gap 414 between it and the needle-storing unit 410 on its left, and having a gap 424 between it and the needle-storing unit 430 on its right, and the other needle-storing units are structured in the same way, having respective gaps.

The needle-storing unit 420 is composed of a mounting pad 421 that adheres a used suture needle, a lid part 422 that covers the mounting pad, and a grip tab 423 in order that the lid part may be grasped when the needle storing unit is to be open/closed. The other needle-storing units possessing the same structure as does the unit 420. In an example method of use, as illustrated at needle-storing unit 410, the lid part 412 is folded over and laid onto the mounting pad 411, encasing a used needle inside, is the same as with the needle storage receptacle of Embodying Mode 1.

Also similar to the needle storage receptacle of Embodying Mode I is that on the lid part of each needle-storing unit, in order from the left, 412 (in FIG. 4, it is laid onto the mounting pad 411), 422, 432, 442, 452, 462, 472, 482, 492, and 402 (in FIG. 4, after 422, 432—402 have been omitted because they are the same as in FIG. 1), the numerals "1," "2," "3," "4," "5," "6," "7," "8," "9," and "10" are printed as display numbers, on the rear side of the lid part of each needle-storing unit. This is so that when the lid part is folded over and stuck onto the mounting pad to seal a needle inside a numeral can be read from the front side.

Further, inasmuch as the film-anchoring portions 404 and 405 on both the left and right ends serve in a similar capacity to those of the needle storage receptacle of Embodying Mode I, an explanation of their roles is omitted.

It should be understood that there are no particularities as to the material, etc. of the sheeting employed in the needle storage receptacles of Embodying Modes 1 and 2. Because the sheeting may be that which is publicly known, an explanation thereof is omitted. For the film-anchoring portions (104 and 105 in FIG. 1; 404 and 405 in FIG. 4) provided on both the left-and-right ends of the needle storage receptacle and utilized in reinforcing, a colored film may be employed. The sheeting employed in the needle-storing units that, by the lid parts being folded over and stuck onto the adhesive surfaces, assume the role of adhesively capturing and storing used needles. This sheeting may be a semitransparent, translucent, white, or an opaque film.

Referring now to FIGS. 5 and 6A-I, an exemplary method that may be implemented using the needle storage receptacles described herein is described. FIGS. 6A-I illustrate a side view of a needle storage receptacle 600 that includes a plurality of needle storage units as discussed in the embodiments herein. In step 500, FIG. 6A-B, a needle storage receptacle 600 is prepared by folding the entire receptacle along a fold line or score 602. The fold can be such that the front-side portion of the lid part 606 is folded toward the mounting pad 608. Following the folding step, the lid part 606 and the mounting pad 608 of each of the needle storage units may be generally perpendicular to each other due to the inherent properties of the needle storage receptacle (i.e., the tendency of the material, such as paper stock, to return to its original position from the folded position); however, it will be understood that a wide range of angles are possible, from, for example, 0° (flat) to 180° (touching). In preferred embodiments, a needle storage receptacle includes a protective material 610 that is easy for a user to remove, such as wax paper or other coated paper. The protective material is placed over the adhesive surfaces 612, 614, and 616 over the length of the needle storage receptacle 600 to prevent the surfaces from adhering to objects prematurely. In one embodiment, the protective material 610 over the surface 612 is a single continuous strip of material, and the protective material 610 over the surfaces 614 and 616 is also a single continuous strip of material. In other embodiments, the surfaces 614 and 616 are covered by individual strips of material. In still other embodiments, a strip of the protective material covers both surfaces 614 and 616, but is divided (e.g., by perforation) between each of the needle storage units. Of course, other embodiments with respect to the configurations of the protective material 610 are also contemplated herein.

Figure 6A:
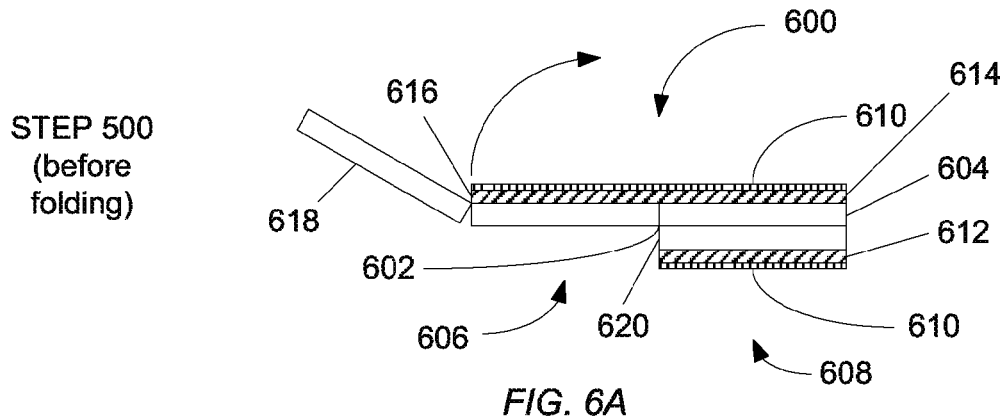
FIGS. 6A-I are illustrations of the exemplary method of FIG. 5.
Figure 6B:
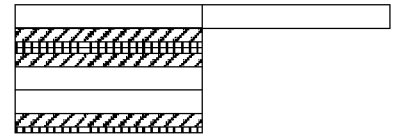
Figure 6C:
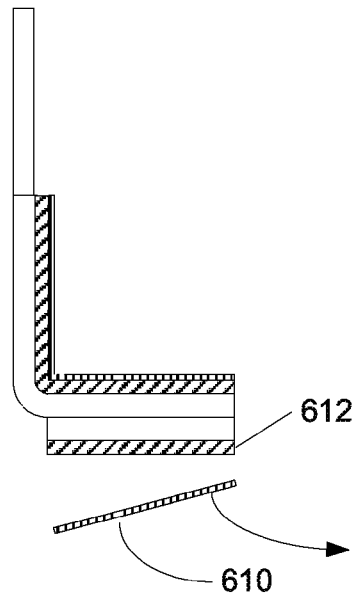
Figure 6D:
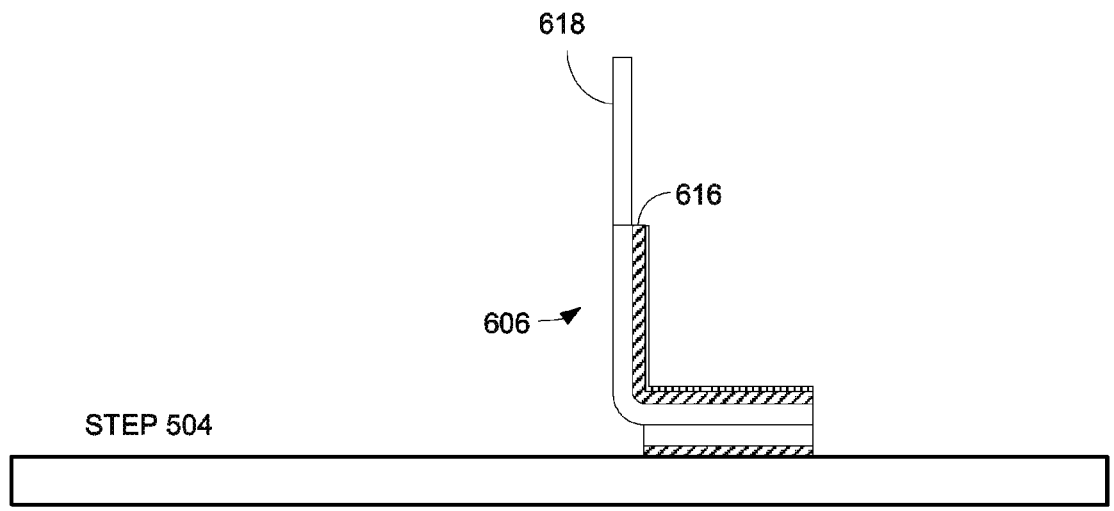

In step 502, FIG. 6C, after the user has released the needle storage receptacle from its folded position and the material properties return the receptacle to a generally perpendicular position as shown, the protective material 610 is removed from adhesive surface 612 over the entire needle storage receptacle in preparation for the needle storage receptacle to be positioned on a table or other mounting surface in a surgery room (or other clinical setting) that is easily accessible by a surgeon or nurse assistant. In step 504, FIG. 6D, the needle storage receptacle is attached to a cloth wrapped block, sterile drape, or other covering on the surgery room surface by way of adhesive surface 612. Accordingly, the adhesive surface 612 will be above and generally on a parallel plane with the table or block. Further, the lid part 606, adhesive surface 616, and grip tab 618 will generally remain at an angle of 90° with the pad, although angles from 0° (flat) to 180° (touching) are possible.

Figure 6E:
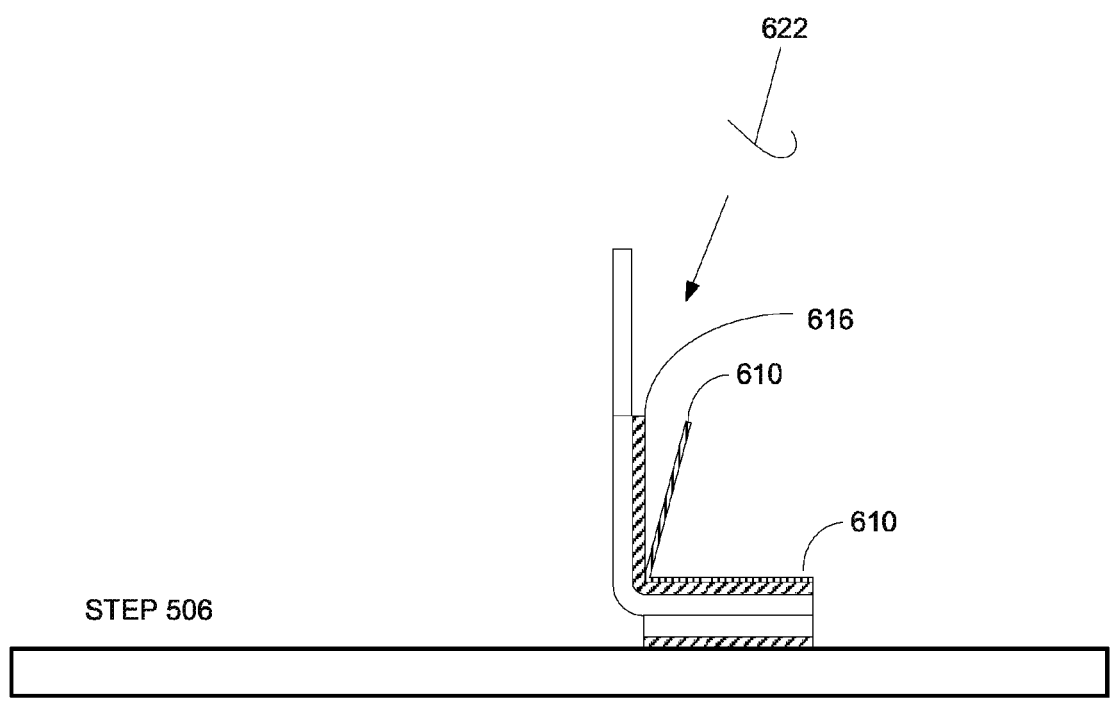
Figure 6F:
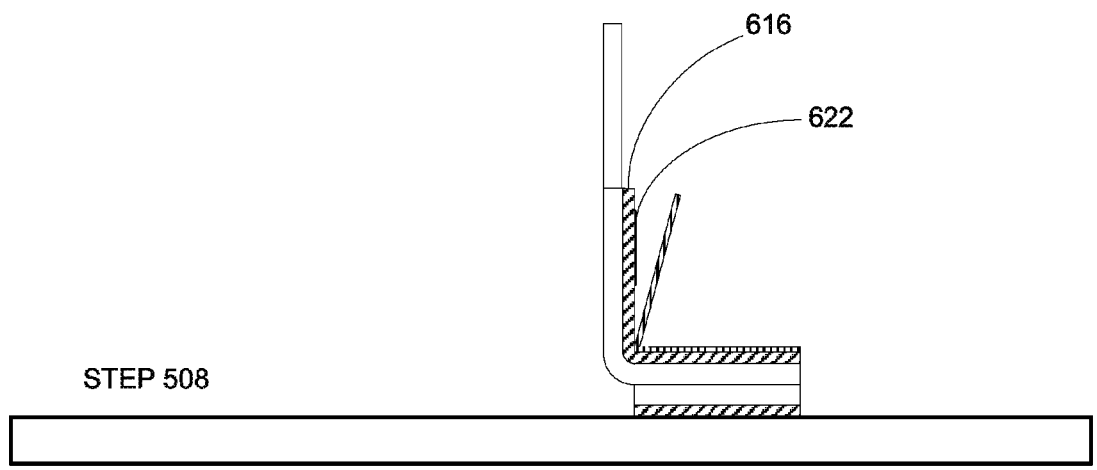
Figure 6G:
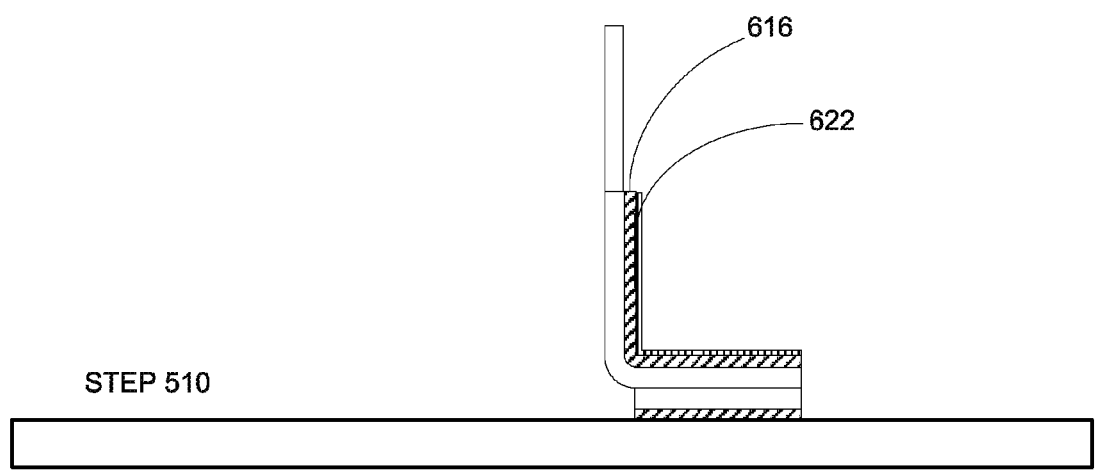

In step 506, FIG. 6E, the protective material 610 of an individual needle storage unit is peeled back slightly from the adhesive surface 616 thereof, and one or more needles 622 are placed into the needle storage receptacle by way of a forceps or other instrument. In step 508, FIG. 6F, the one or more needles 622 are between the adhesive surface 616 and the protective material 610, and may be adhered to the adhesive surface. After placement of a needle into this area between the adhesive surface 616 and the protective material 610 (and in many cases directly on the adhesive surface 616), a clinician may wish to push the protective material back toward the adhesive surface 616 using a forceps or other instrument to ensure that the needle(s) remain therein, retrieve another needle, and then pull the protective material back to insert another needle into the same needle storage unit. In step 510, FIG. 6G, after the desired number of needles are positioned between the adhesive surface 616 and the protective material 610 in a particular needle storage unit, the protective material 610 is pressed against the adhesive surface to effectively trap the needle(s) 622. In one embodiment, steps 506-510 are repeated for each of the needle storage units of the needle storage receptacle 600.

Figure 6H:
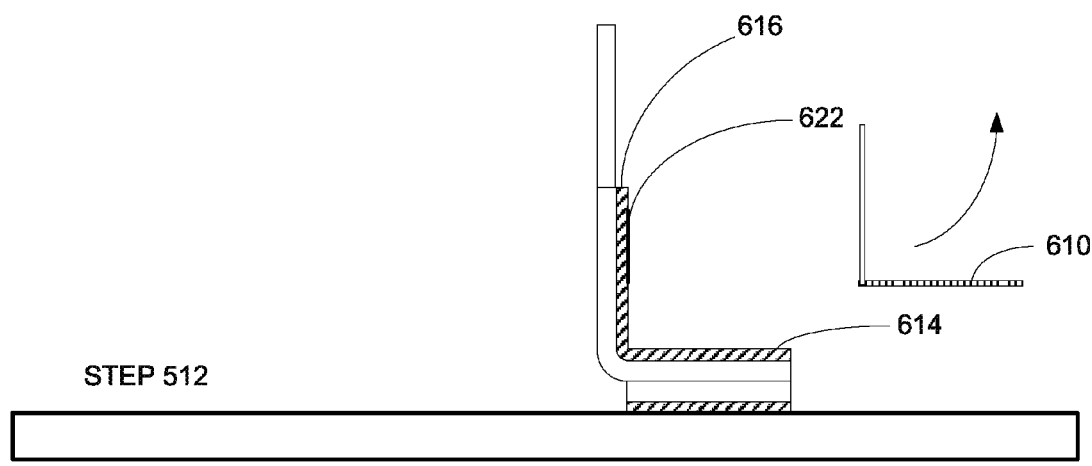
Figure 6I:
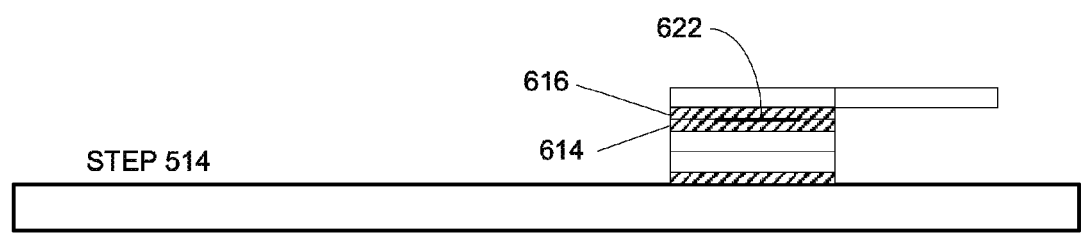

After the desired number of needle storage units have been utilized to insert one or more needles between the adhesive surface 616 and the protective material 610, in step 512, FIG. 6H, the protective material 610 is removed from both the adhesive surface 614 and the adhesive surface 616 of the needle storage units either individually or collectively along the length of the needle storage receptacle 600. In some embodiments, the protective material 610 may be perforated such that each of the needle storage units may be uncovered separately. In step 514, FIG. 6I, the adhesive surface 616 is folded down onto the adhesive surface 614 to permanently trap the needle(s) 622 for disposal.

Figure 5:
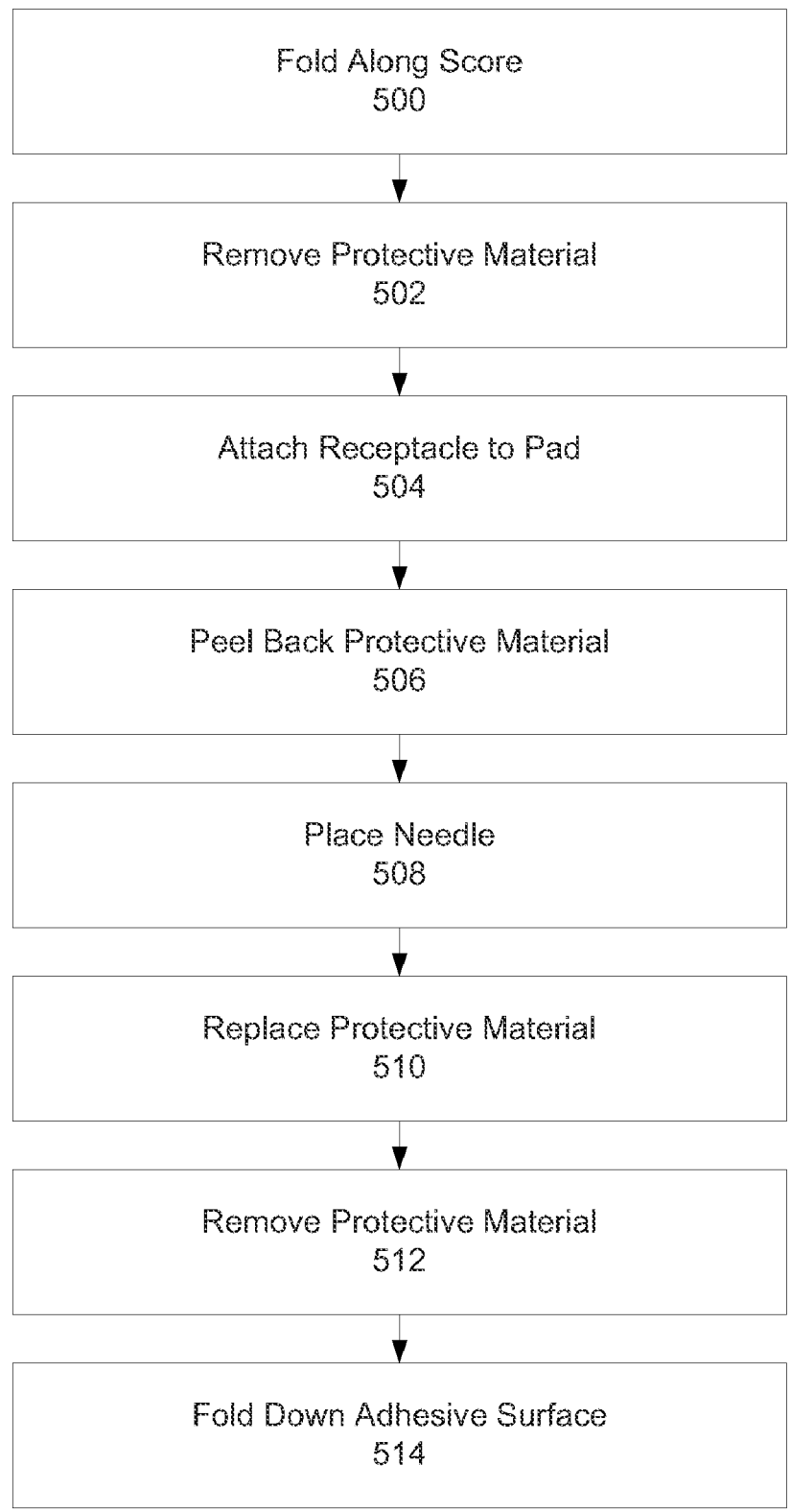
FIG. 5 is a block diagram illustrating an exemplary method that may be implemented using the needle storage receptacles described herein is described.

It will be understood that the example method illustrated in FIG. 5 may be implemented for each of the embodiments described herein. Additionally, as illustrated in FIGS. 6A-I, the mounting pad 608 portion is somewhat thicker than the lid part 606 portion. This is because the mounting pad 616 includes adhesive surfaces 612 and 614 on both sides of the underlying layers, because each adhesive surface 612 and 614 may include a protective layer 610, and because the mounting pad includes the front-side portion 604 and the underside portion 620. It will be understood that, in some embodiments, the thickness of the underlying material forming the lid part 606 and the mounting pad 608 can be generally the same thickness, rather than having the front-side portion 604 and the underside portion 620 form an underlying layer of the mounting pad 608 that is thicker than the underling layer of the lid part 606.

Although the invention has been described in conjunction with specific embodiments thereof, it should be evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for disposing of suture needles, comprising:
preparing a needle storage receptacle by folding the receptacle along a fold line;
removing a first strip of protective material from a first adhesive surface of the needle storage receptacle;
attaching the needle storage receptacle to a mounting surface by positioning the first adhesive surface against the mounting surface;
peeling back a second strip of protective material from a second adhesive surface of a needle storage unit and placing a suture needle between the protective material and the second adhesive surface;
removing the second strip of protective material from the second adhesive surface and also from a third adhesive surface adjacent the second adhesive surface; and
folding the second adhesive surface into contact with the third adhesive surface to permanently trap the needle.

2. The method according to claim 1, further comprising, following the peeling back step, pressing the protective material back onto the second adhesive surface and retrieving a second suture needle for insertion between the protective material and the second adhesive surface of the needle storage unit.

3. The method according to claim 1, wherein the protective material over the second adhesive surface and third adhesive surface is perforated between each needle storage unit of a plurality of needle storage units.

4. The method according to claim 1, wherein following the preparing step, but before the removing step, a lid part of the needle storage receptacle and a mounting pad of the needle storage receptacle form an angle of about 90°.

5. The method according to claim 1, wherein the first adhesive surface is located on an underside portion of the needle storage receptacle, and the second and third adhesive surfaces are located on a front-side portion thereof, the third adhesive portion located on the same side of the fold line as the first adhesive portion.

* * * * *